United States Patent
Avramescu et al.

(10) Patent No.: US 9,243,998 B2
(45) Date of Patent: Jan. 26, 2016

(54) RESONANT PHOTO ACOUSTIC SYSTEM

(75) Inventors: Viorel Avramescu, Bucharest (RO); Mihai Gologanu, Bucuresti (RO); Daniel Youngner, Maple Grove, MN (US); Bob Jon Carlson, Brooklyn Park, MN (US)

(73) Assignee: Honeywell International Inc., Morris Plains, NJ (US)

( * ) Notice: Subject to any disclaimer, the term of this patent is extended or adjusted under 35 U.S.C. 154(b) by 71 days.

(21) Appl. No.: 13/524,407

(22) Filed: Jun. 15, 2012

(65) Prior Publication Data

US 2013/0008230 A1   Jan. 10, 2013

Related U.S. Application Data

(60) Provisional application No. 61/505,427, filed on Jul. 7, 2011.

(51) Int. Cl.
*G01N 21/17* (2006.01)

(52) U.S. Cl.
CPC .... *G01N 21/1702* (2013.01); *G01N 2021/1704* (2013.01); *G01N 2021/1708* (2013.01)

(58) Field of Classification Search
CPC .............. G01N 21/17; G01N 21/1702; G01N 2021/1708; G01N 2021/1704
USPC ........................................................ 73/24.02
See application file for complete search history.

(56) References Cited

U.S. PATENT DOCUMENTS

| | | | | |
|---|---|---|---|---|
| 4,764,244 A | * | 8/1988 | Chitty et al. | 216/20 |
| 4,817,413 A | * | 4/1989 | Asano et al. | 73/24.02 |
| 5,187,367 A | * | 2/1993 | Miyazaki et al. | 850/57 |
| 6,370,954 B1 | * | 4/2002 | Zerbini et al. | 73/514.01 |
| 6,564,639 B1 | * | 5/2003 | Hatanaka et al. | 73/504.16 |
| 6,662,627 B2 | | 12/2003 | Arnott et al. | |
| 7,263,871 B2 | | 9/2007 | Selker et al. | |
| 7,765,871 B2 | | 8/2010 | Riddle | |
| 2011/0072886 A1 | | 3/2011 | Caneau et al. | |
| 2011/0088453 A1 | | 4/2011 | Nicoletti et al. | |
| 2011/0094291 A1 | | 4/2011 | Gidon et al. | |
| 2011/0290002 A1 | | 12/2011 | Heidrich et al. | |
| 2012/0151995 A1 | | 6/2012 | Schade et al. | |

FOREIGN PATENT DOCUMENTS

| | | | | | |
|---|---|---|---|---|---|
| DE | 102008047658 | | * | 1/2010 | ............. G01N 21/17 |
| DE | 102009029002 B3 | | | 1/2011 | |
| EP | 2246688 A1 | | * | 11/2010 | |

OTHER PUBLICATIONS

"European Application Serial No. 12173903.1, Office Action mailed Nov. 19, 2012", 9 pgs.

(Continued)

*Primary Examiner* — Daniel S Larkin
*Assistant Examiner* — Irving A Campbell
(74) *Attorney, Agent, or Firm* — Schwegman Lundberg & Woessner, P.A.

(57) ABSTRACT

A device includes a resonator having an oscillating portion with dimensions chosen to lead to a desired resonant frequency. A light source is positioned to provide light along the length of the oscillating portion at a specific wave length. A detector detects a change in oscillation of the resonator responsive to the wave pressure produced by the light source heating a gas. The light source is modulated with a frequency the same as the resonant frequency of the resonator.

14 Claims, 7 Drawing Sheets

(56) References Cited

OTHER PUBLICATIONS

"European Application U.S. Appl. No. 12173903.1, Response filed Mar. 28, 2013 to Office Action mailed Nov. 19, 2012", 10 pgs.

"European Application Serial No, 12173903.1, European Search Report mailed Nov. 6, 2012", 4 pgs.

Kuusela. T., et al., "Photoacoustic gas detection using a cantilever microphone and III-V mid-IR LEDs". *Vibrational Spectroscopy, 51*, (2009), 289-293.

\* cited by examiner

RESONANT PHOTO ACOUSTIC SYSTEM

RELATED APPLICATION

This application claims priority to U.S. Provisional Application Ser. No. 61/505,427 (entitled Silicon Resonant Photo-Acoustic System (SRPAS), filed Jul. 7, 2011) which is incorporated herein by reference.

BACKGROUND

Photo acoustic spectroscopy (PAS) is a widely used method for trace gas detection. It is based on the photo acoustic (PA) effect, i.e. the conversion of light to sound in all materials (solids, liquids and gases). It applies to many chemical compounds, and, unlike conventional absorption spectroscopy, its sensitivity scales inversely with the volume of the sampling chamber.

To date, limited research has been done to demonstrate the feasibility of a miniaturized photo acoustic sensor. In order to realize the advantage of photo acoustic sensor miniaturization, light sources and detectors of comparable size are required. In order to achieve spectrometric performances, lasers are typically suggested as light sources. In recent years a large effort has been paid to develop semiconducting lasers (VCSEL, DFB, QCL) for spectral ranges of interest.

A "classical" spectrometric PAS has, beyond the laser, a chamber and a detector. The detector is usually in a form of a microphone. To increase the sensitivity of the system, a non-resonant chamber may be replaced with a resonant-one that is designed to have a resonant frequency equal to the modulation frequency of the laser. Thus, the amplitude of the pressure wave generated inside the chamber is amplified by the chamber that works at resonance.

A second approach to increase the sensitivity is to replace the microphone with an acoustic resonant detector. A solution developed by researchers from Rice University uses a quartz tuning fork (QTF) from an electronic watch (QEPAS—Quartz Enhanced Photo Acoustic Spectroscopy) as a resonant detector. In such a system the laser (chosen to fit an absorption line of the gas to be detected) is additionally modulated at a frequency related to the resonant frequency of the tuning fork. As the laser beam passes between and transverse to the two prongs of the fork, the laser light is absorbed by the target gas which heats up and creates a pressure wave. These pressure waves impinge on the prongs of the QTF which start to move in opposite directions. These deflections are finally converted by a piezoelectric effect to a current with an amplitude proportional to the concentration of the target gas.

The advantages of QEPAS systems are its small dimensions, high sensitivity and the elimination of the detection chamber replaced by the gap between the prongs of the QTF. While this concept has been proven in a laboratory setting, it seems difficult or impossible to adapt it to large scale manufacturing and to reap the benefits of further miniaturization.

SUMMARY

A device includes a resonator having an oscillating portion with a length and a width. A light source is positioned to provide light along the length of the oscillating portion. A detector detects a change in oscillation of the resonator responsive to the light source heating a gas.

A method includes providing light adjacent to a length of a micro electromechanical systems (MEMS) resonant oscillator, exposing a gas to be detected to the light to create a pressure wave, and detecting oscillation of the oscillator responsive to the pressure wave.

A sensor includes a device formed on a silicon on insulator (SOI) wafer. A microelectromechanical single crystal resonator is released from the device side of a silicon on insulator (SOI) wafer. An optical fiber light source provides light along the length of the oscillating portion in a cavity formed in the device wafer, the light having a frequency tuned to a resonant frequency of the resonator and to an absorption line of a gas to be detected. A handle wafer supports the device wafer and the optical fiber light source. A detector is coupled to detect a change in oscillation of the resonator responsive to the light source heating the gas.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
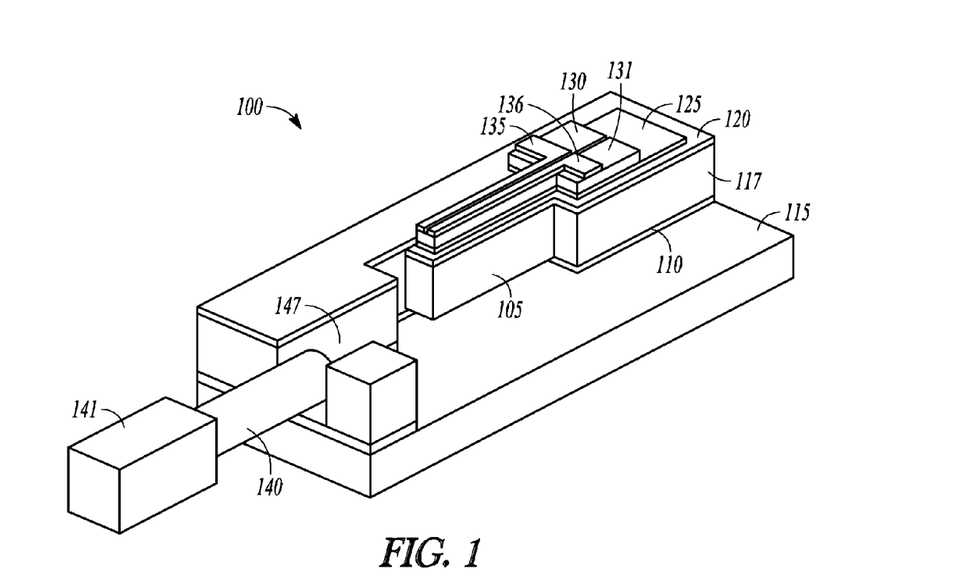
FIG. 1 is a perspective block diagram view of a photo acoustic sensor according to an example embodiment.
Figure 2:
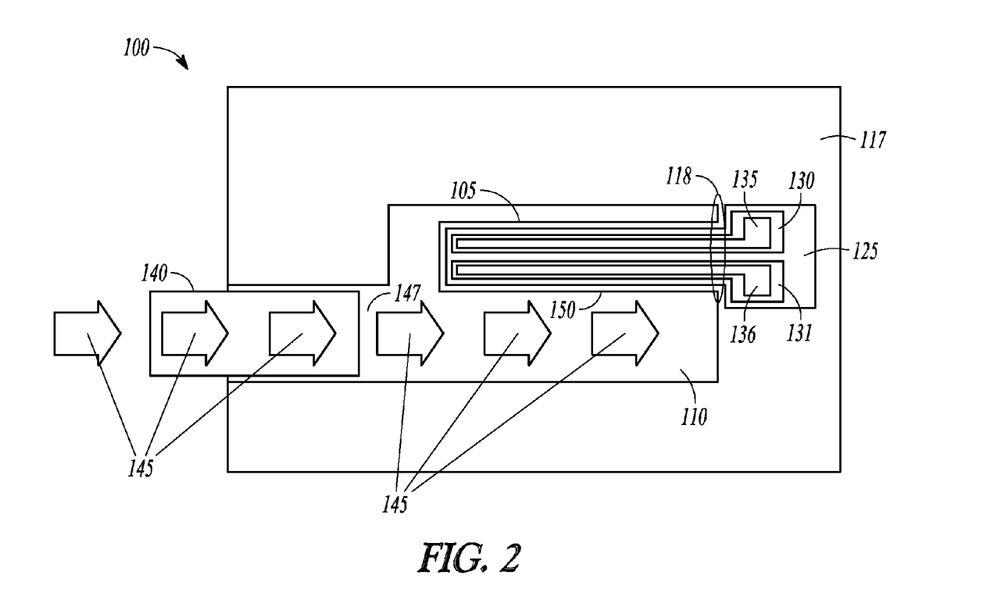
FIG. 2 is a top block diagram view of the example photo acoustic sensor of FIG. 1.

FIG. 1 is a perspective block diagram view of a photo acoustic sensor indicated generally at 100 according to an example embodiment. A top block diagram view of photo acoustic sensor 100 is illustrated in FIG. 2 with reference numbers consistent with the reference numbers in FIG. 1. A resonator 105 is supported by a buried oxide layer 110 formed on a handle wafer 115. In one embodiment, the resonator 105 includes a cantilevered beam formed from a device layer 117 and suspended above the handle wafer 115, allowing it to vibrate at a resonant frequency of the beam. The suspension of the resonator 105 beam may be accomplished by removing the oxide layer 110 from under the resonator 105 beam, and in further embodiments, etching at least a portion of the handle wafer 115 beneath the resonator 105 beam. The beam may be anchored to the handle wafer 115 as indicated at an anchor leg 118.

In one embodiment, the resonator 115 may include a further oxide layer 120 with a first electrode 125 supported by the oxide layer 120. The first electrode 125 may be ground electrode in one embodiment. A piezoelectric layer 130, 131 is supported by the first electrode 125 in one embodiment. The piezoelectric layer may be a single layer or may be broken into separate portions as indicated. Electrodes 135, 136 may be formed over piezoelectric layers 130, 131 respectively. If the piezoelectric layer is a single layer, one electrode 135 may be utilized.

In one embodiment, a laser light source 140, such as an optical fiber 140 coupled to a semiconductor laser 141, is coupled to provide light indicated by arrows 145 in a channel 147 along a length 150 of the resonator 125 beam to heat a gas proximate the resonator in the path of the light and cause the resonator to move responsive to pressure waves created along the length 150 of the beam.

In one embodiment, microelectromechanical systems (MEMS) may be used to manufacture the sensor 100 with the handle wafer and device wafer being formed of a semiconductor material such as silicon, germanium, or other suitable material. The sensor may be a piezoelectric transducer single crystal silicon micromechanical resonator 105. In order to obtain an electric signal from the resonator 105, layers 130, 131 may be formed of zinc-oxide (ZnO) layer or another piezoelectric layer is deposited on the silicon device layer of a SOI wafer 117 to obtain high Q resonators with low impedance. MEMS techniques allow the hybrid integration of a semiconductor laser with the sensor 100 as well as accurate alignment of the optic fiber 140 (which provides the light from the laser 141) with the silicon resonator 105.

Mechanisms of energy losses in resonant silicon structures at ambient pressure include, air friction, air compression, air squeezing between beam and substrate, thermo elastic damping, acoustic wave reemission, and structural losses through anchors. Anchor losses can be highly reduced by using a design where the resonant system has a fixed center of mass.

The starting material for the resonator in one embodiment is the silicon-on-insulator (SOI) wafer 117. The device wafer thickness is similar in range to the diameter of the fiber 140. Laser 141 is shown as a block, and may be constructed and supported on the same handle wafer 115, or a separate wafer in various embodiments. In one embodiment, the laser provides light having a wave length tuned on a specific absorption line of a gas to be detected. An array of sensors 100 with lasers tuned to absorption lines of multiple gases to be detected may be formed on a single handle wafer and device wafer in one embodiment. Each resonator 105 may also have dimensions selected to obtain a resonant frequency the same or substantially the same as a selected absorption frequency.

The optical fiber 140 may be embedded in the channel 147 etched in the device wafer 117. The light 145 coming out from the core of the fiber 140 travels along the resonator 105 beam. This alignment can be easily achieved by properly inserting the fiber inside the channel 147. Further fixing of the fiber 140 may be realized with appropriate glue or other adhesive.

Figure 3A:
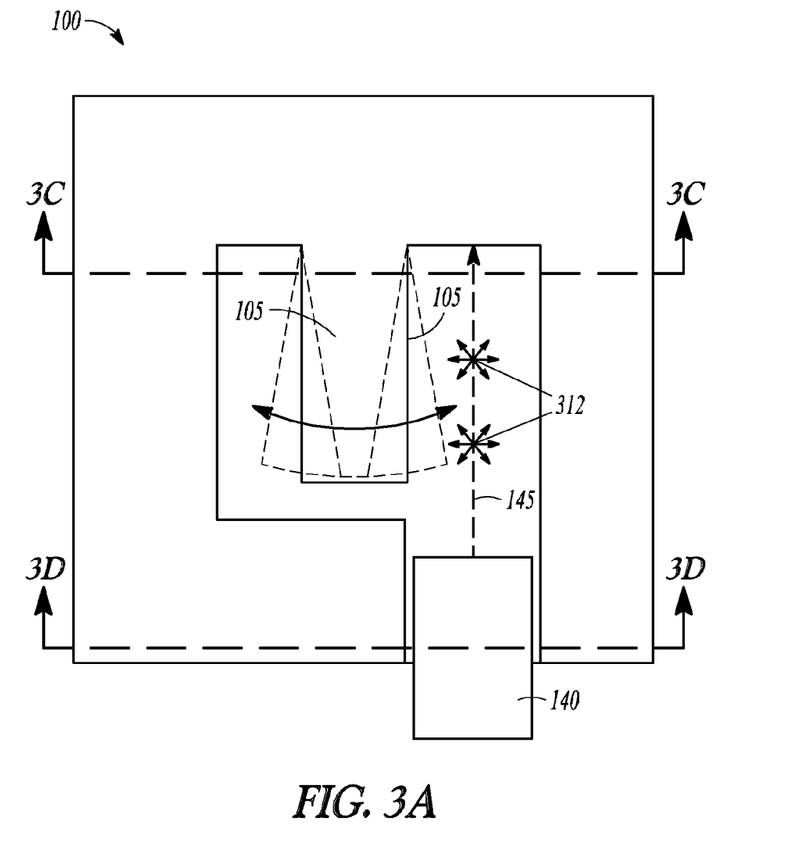
FIG. 3A is a top block diagram view showing selected layers of a photo acoustic sensor according to an example embodiment.
Figure 3B:
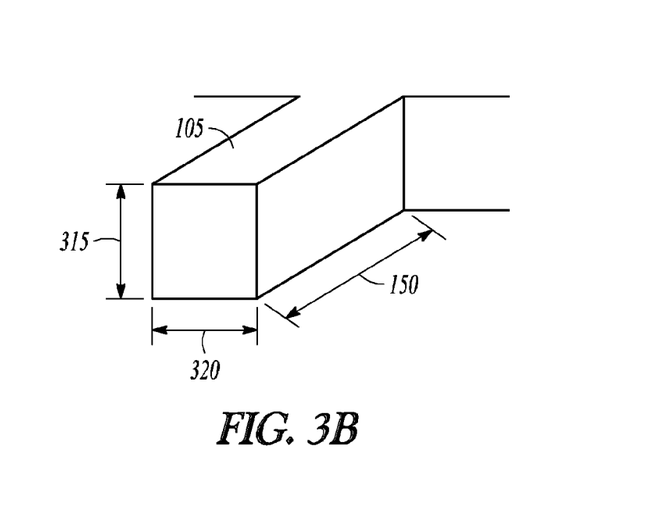
FIG. 3B is a perspective block diagram view illustrating a beam resonator of a photo acoustic sensor according to an example embodiment.
Figure 3C:
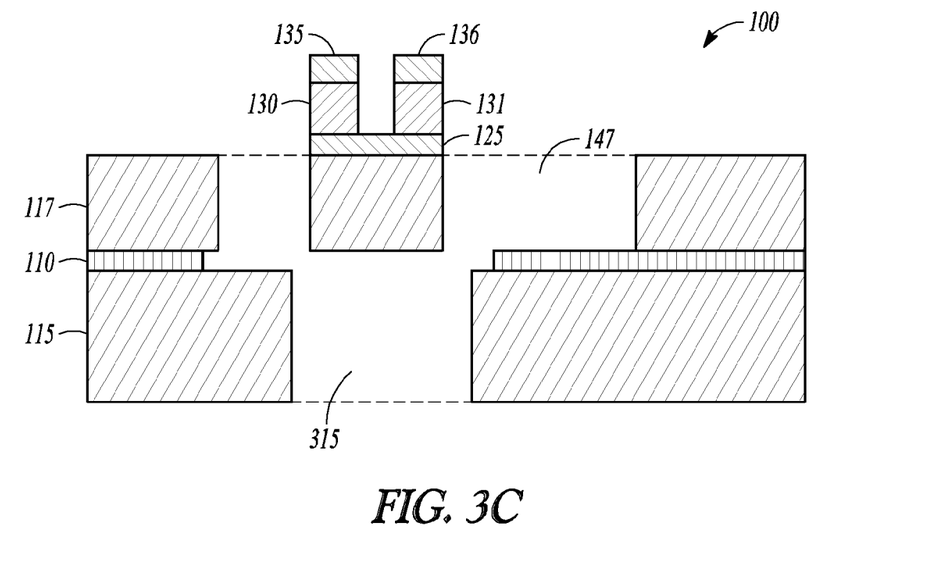
FIG. 3C is a cross section block diagram view taking along line 3C-3C of FIG. 3A according to an example embodiment.
Figure 3D:
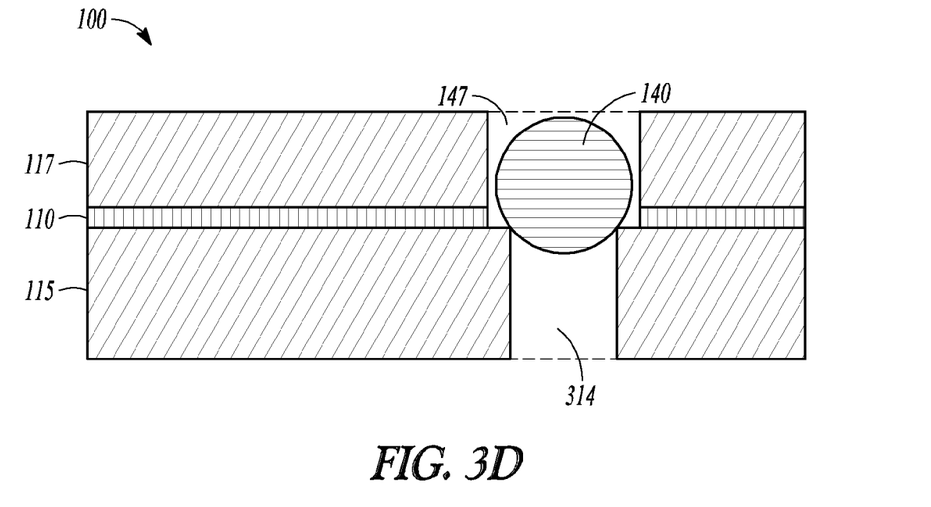
FIG. 3D is a cross section block diagram view taking along line 3D-3D of FIG. 3A according to an example embodiment.

FIG. 3A is a top block diagram view showing selected layers of the photo acoustic sensor 100. FIG. 3B is a perspective block diagram view illustrating the resonator 105 beam. FIG. 3C is a cross section block diagram view taking along line 3C-3C of FIG. 3A. FIG. 3D is a cross section block diagram view taking along line 3D-3D of FIG. 3A. In sensor 100, the light beam 145 coming out from the fiber 140 can be seen as multiple punctual heat sources 312 giving rise to higher acoustic pressure that impinges on the resonator 105 in the form of a cantilever. In prior tuning fork designed, heating of gas occurred at a point between tines of a tuning fork, resulting in a very small portion of the tuning fork being subjected to pressure waves. In the present embodiments, the fiber 140 is positioned such that light runs adjacent to and along a length 150 of the resonator beam 10, providing heat along that length 150, a much longer distance, resulting in more force being generated on the resonator due to more gas being heated.

The acoustic pressure—generated by the local gas heating due to the absorption of the energy from the laser beam on a specific wave length—decays abruptly when going away from the light beam. In one embodiment, the width 320 of the beam is designed to provide enough pressure drop across the width (W) of the cantilever in order to have enough force to move it. Working with silicon provides a large design latitude for an optimal shape of the resonator, allowing selection of dimensions to create a desired pressure drop between sides of the cantilever.

In one embodiment, the laser is modulated with same frequency as the resonant frequency of the mechanical structure, the resonator 105 beam in order to take advantage on the amplification of the displacement at resonance. In further embodiments, different sensing techniques (capacitive, piezorezistive, optical, piezoelectric) may be used for the detection of the displacement of the resonator 105 beam. The piezoelectric effect provides for high electrical output and technological simplicity of implementation.

In one embodiment, a thin layer of piezoelectric material 130, 312 is deposited by an appropriate technique directly on silicon or on a previously deposited and patterned metal layer 125 that act as electrical ground. ZnO or AlN are two different piezoelectric layers that may be used to detect the displacement of the silicon resonator. In both situations the deposition of the piezoelectric layer may be realized by sputtering.

Sputtering is not the only method for the realization of the piezoelectric layers. Sol-gel or CVD methods, or any other suitable method may alternatively be used. The piezoelectric layers are not limited to ZnO or AlN. PZT may also be used due to its superior electromechanical coupling coefficient. Piezoelectric layers formed of different materials may be used in further embodiments.

The piezoelectric layer is situated on top of the silicon resonant structure in one embodiment. Whatever structure is used it has a structure such as a beam that bends under the photo acoustic pressure. In general, if the piezoelectric layer is deposited over the entire width of the beam, the electric charge generated, due to the strain, on different position can have different polarities. A proper choice of the vibration mode as well as the splitting of the piezoelectric layer in two strips 130, 131 along the length of the beam—as shown in 3C-3C cross section in FIG. 3C may be used to prevent charge compensation for the two resulting strips. In general one strip will collect positive electrical charges and the other negative electrical charges. By subtracting the two signals the output signal may be doubled.

Moreover, having two sensing lines 135, 136 on the resonator beam helps the detection and a periodical calibration of the resonant frequency of the structure. Thus, the resonant beam can be mechanically driven using one piezoelectric strip 130 by applying AC voltage on the first piezoelectric strip between the ground electrode 125 and one of the upper electrodes 135. The mechanical movement may be detected by measuring the voltage on the second piezoelectric strip 132 between the second upper electrode 136 and same ground electrode 125.

A proper design of the silicon resonators takes into account the different sources of energy loss. These losses have impact on the quality factor (Q) of the resonator. The losses may be minimized in one embodiment to obtain a Q-factor higher than 1000 in air for structures with resonant frequencies in the range of the tens of KHz. High Q-factor is desirable for a good sensitivity of sensor 100.

Air friction, air compression, air squeezing between beam and substrate, thermo elastic damping, acoustic wave reemission, structural losses through anchors are the major energy loss sources in these resonators.

The channel 147 for the optical fiber 140 as well as the resonator 105 beam itself may be etched in the device wafer 117 by DRIE (deep reactive ion etching) or other means. DRIE stops at the interface between the device wafer 117 and the handle wafer 115 due to the buried oxide layer (BOX) 110. Another advantage of using DRIE is the very good aspect ratio of the etched structures. Thus the obtained walls are quasi vertical that helps the photo acoustic effect.

In some embodiments, a V-groove obtained by anisotropic etching of silicon may be used for precise positioning of the fiber. It is difficult to combine two types of etching—wet and dry—during the realization process of the resonator and the channel. DRIE provides an accurate and appropriate pattern for the photo acoustic effect.

Moreover DRIE is independent to the crystallographic orientation of the handle wafer 115 and device wafer 117 in a SOI stack by contrast to wet etching that is dependent on crystallographic orientation. Better positioning of the fiber can be obtained if the handle wafer 115 is etched through as indicated at 314 in a separate process as it is shown in FIG. 3D. However the final fixing of the fiber optic may be performed with appropriate glue as previously described.

The main part of the device is the silicon resonator. It may be obtained during the same etching process as for the channel that is used to fix the fiber. Losses due to air friction between the beam and the handle wafer 115 may be avoided by etching the handle wafer under the beam as indicated at 315 in FIG. 3C.

One loss occurs through the anchor of the structure e.g. the leg 118 of the cantilever. A structure with improved mechanical performances is represented by a tuning fork realized using same technology.

Figure 4A:
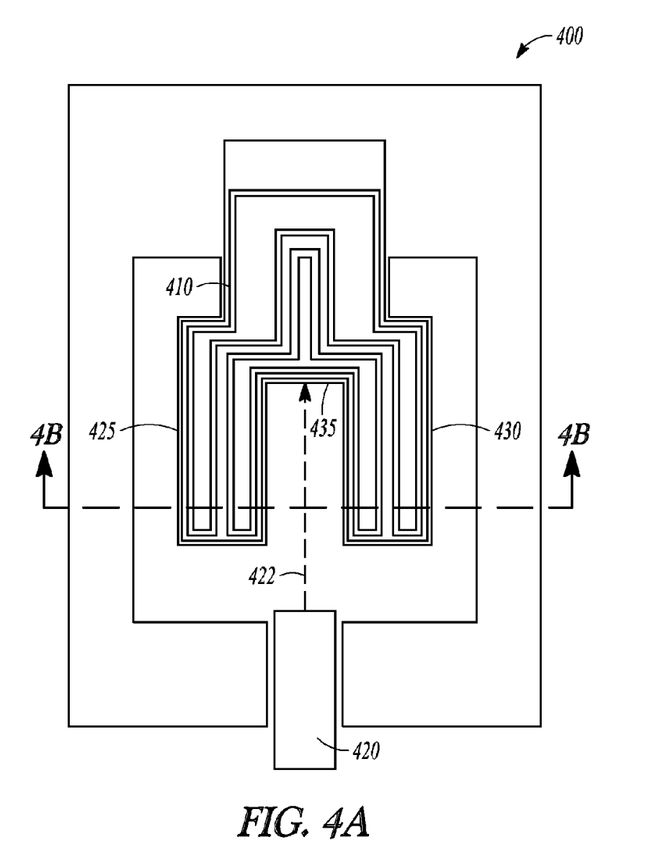
FIG. 4A is a top block diagram view of a photo acoustic sensor utilizing a tuning fork according to an example embodiment.
Figure 4B:
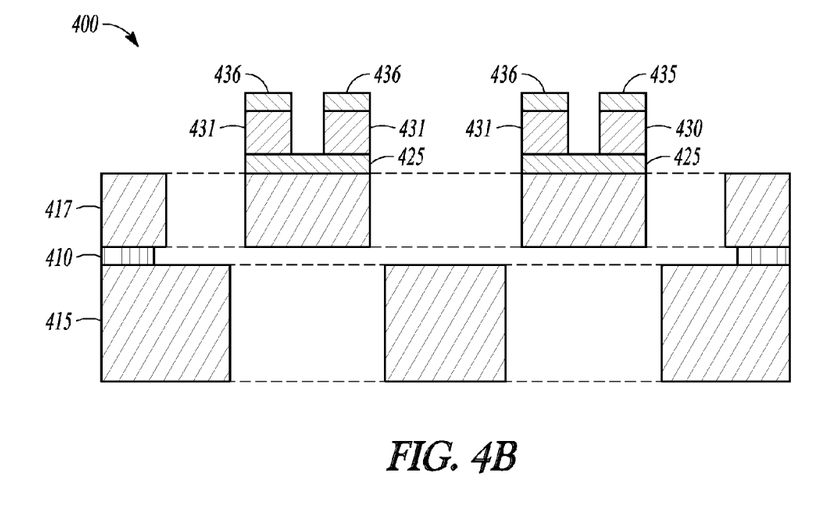
FIG. 4B is a cross section block diagram view taken along line 4B-4B of FIG. 4A illustrating selected layers of a photo acoustic sensor according to an example embodiment.

FIG. 4A is a top block diagram view of a photo acoustic sensor 400 utilizing a tuning fork 410 according to an example embodiment. FIG. 4B is a cross section block diagram view taken along line 4B-4B of FIG. 4A illustrating selected layers of the photo acoustic sensor 400. Sensor 400 may be used to illustrate effects of thermo elastic dumping in silicon. In one embodiment, a light source such as fiber 420 may provide light illustrated as broken line 422 along and between tines 425, 430 of tuning fork 410. In this embodiment, the heat source is no longer a point as in prior tuning fork type designs, an entire line. However, even if silicon doesn't absorb IR radiation (that is mainly used for this photoacoustic gas detection application) it is expected a heat-up the anchor 435 of the tines. Layers illustrated in FIG. 4B include layers similar to those in previous embodiments with handle wafer 415, oxide 410, device wafer 417, electrode 425, piezoelectric layers 430, 431 and electrodes 435, 436.

Figure 5:
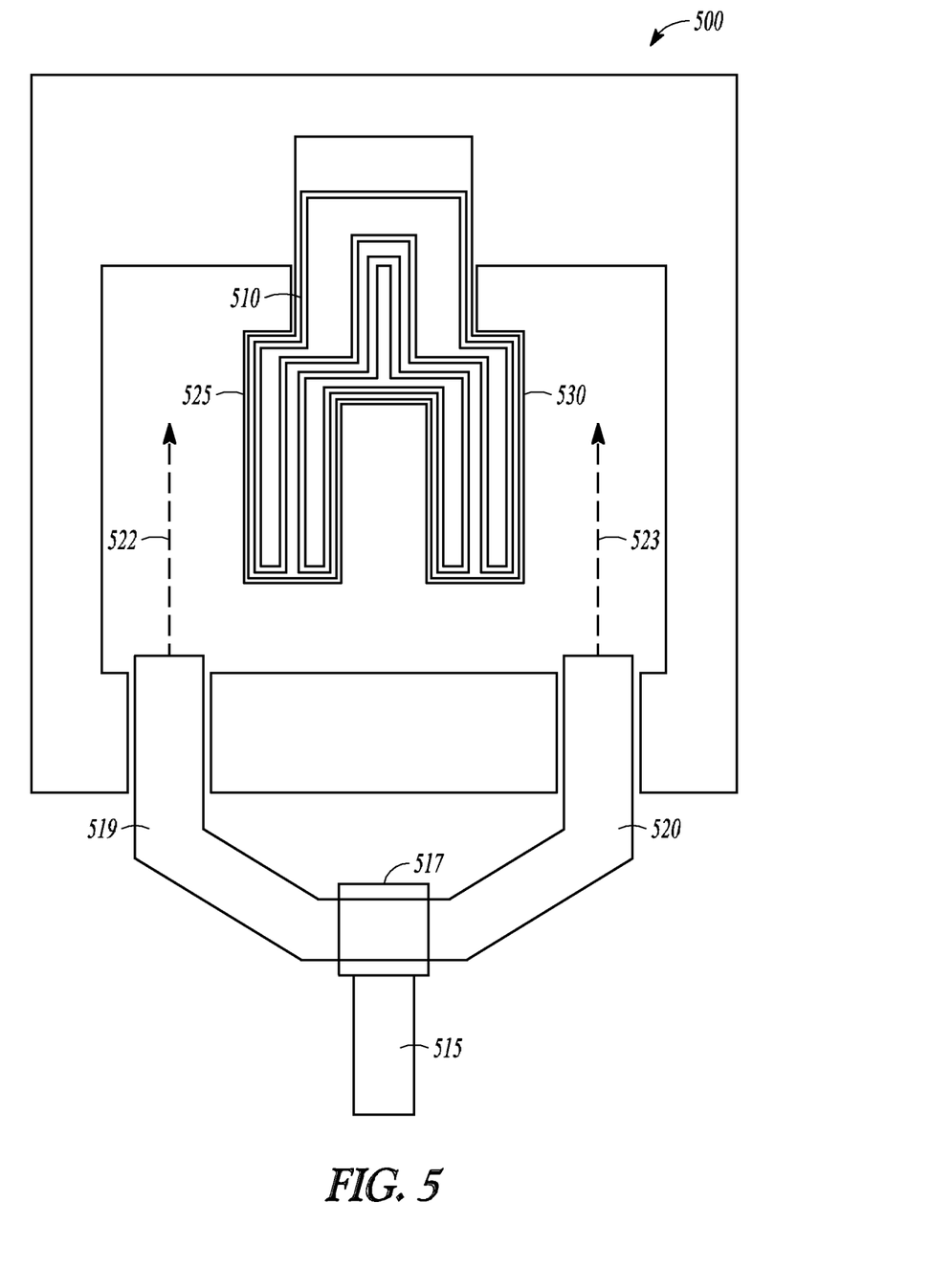
FIG. 5 is a top block diagram view of a photo acoustic sensor utilizing a tuning fork and two laser beams according to an example embodiment.

In order to prevent this heating and to keep the advantage of having two branches to prevent the losses through the anchor two further embodiments are described. FIG. 5 is a top block diagram view of a photo acoustic sensor 500 utilizing a tuning fork 510 and a light source 515 that is split via a beam splitter 517 into two light sources 519, 520 providing respective laser beams indicated at broken lines 522, 523. The light from the two fibers 519, 520 passes along outside the length of both tines 525, 530 of the tuning fork 510. In this way the light doesn't hit the anchor, preventing heating of the tuning fork other than via the gas.

Figure 6A:
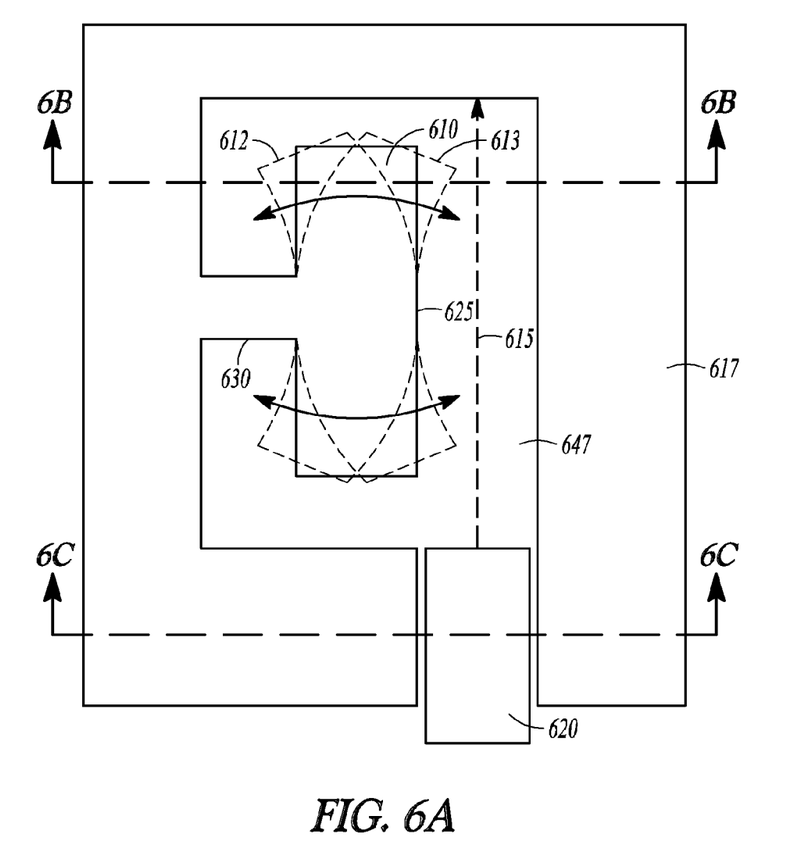
FIG. 6A is a top block diagram view of a photo acoustic sensor utilizing a T-shaped resonator according to an example embodiment.
Figure 6B:
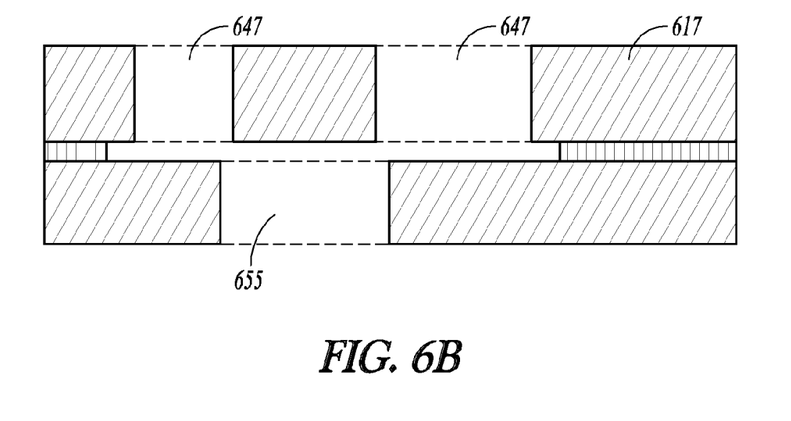
FIG. 6B is a cross section block diagram view of the photo acoustic sensor of FIG. 6A taken along lines 6B-6B according to an example embodiment.
Figure 6C:
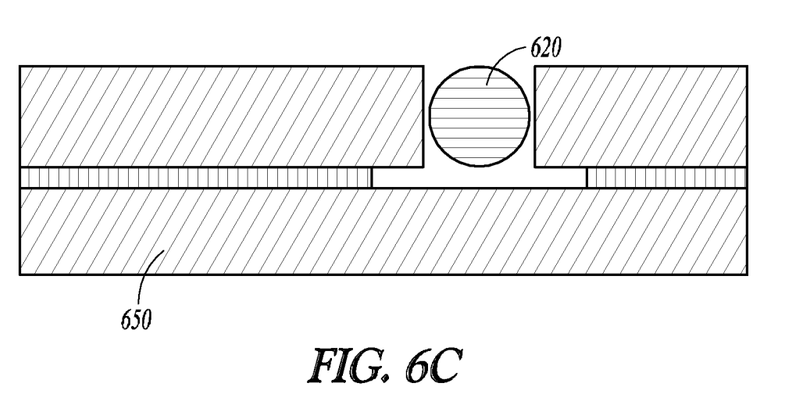
FIG. 6C is a cross section block diagram view of the photo acoustic sensor of FIG. 6A taken along lines 6C-6C according to an example embodiment.
Figure 6D:
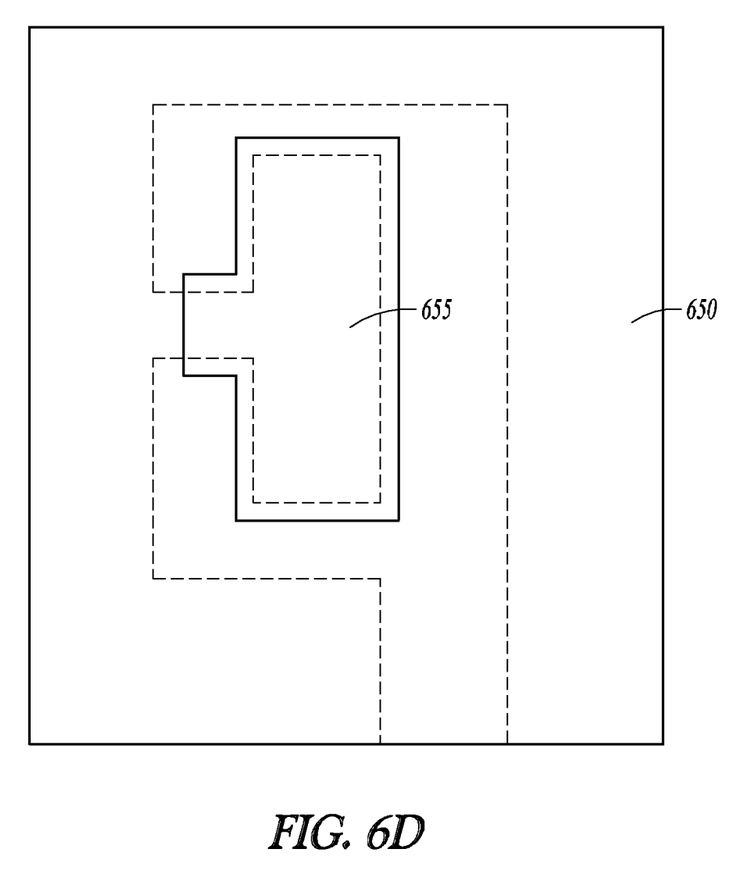
FIG. 6D is a bottom block diagram view of the sensor of FIG. 6A.

A further embodiment is illustrated at 600 in FIGS. 6A, 6B, 6C, and 6D. FIG. 6A is a top block diagram view of photo acoustic sensor 600 utilizing a T-shaped resonator 610. FIG. 6B is a cross section block diagram view of the photo acoustic sensor 600 taken along lines 6B-6B, FIG. 6C is a cross section block diagram view of the photo acoustic sensor 600 of FIG. 6A taken along lines 6C-6C, and FIG. 6D is a bottom block diagram view of the sensor of FIG. 6A. The resonator 610 moves between positioned indicated by broken outlines 612 and 613 responsive to heating of gas by light 615 from a laser source 620 that travels along a length of a top 625 of the "T" shaped resonator 610. Low losses occur from an anchor 630 of the resonator, and low heating-up occurs because the laser does not impinge on the resonator 610.

The silicon resonator 610 has T-shape configuration with two branches. The same technology may be used to release the T-shape resonator as for the cantilever resonator and the tuning fork. The light 615 from only one fiber 620 passes along the two branches or adjacent to and along the length of the top 625 of the "T" structure and doesn't hit the anchor. As indicated in FIG. 6B, a channel 647 in the device wafer 617 extends around the top 625 of the resonator. Further, the handle wafer, indicated at 650 may also be etched beneath the resonator as indicated at 655 to reduce losses due to air friction between the resonator and the handle wafer side from the SOI wafer.

In one embodiment, the beam of the light emitted from the fiber is fairly uniform. A large divergence may be avoided by ending the fiber with a lens 630 that focuses the emitted light.

However the dimensions of the resonant structures are quite small for many desired working frequencies and the ordinary low divergence of the light emitted from the fiber doesn't affect the ability to sense gas heating.

For example a cantilever having a length (L) of 3 mm and a width (W) of 300 microns has a useful mode of vibration for photo-acoustic application with a resonant frequency around 40 kHz. The same frequency is associated with a vibration mode useful for photo-acoustic application for both tuning-fork and T-shape resonators with branches having the same dimensions as the resonators.

In the above mentioned embodiments, the resonant structures may be finally released by removing the buried oxide in SOI wafer. This may be realized by wet etching. However releasing by wet etching a structure that has a width W 320 of 300 microns may be a long process. Moreover, after removing the oxide, air squeezing and air friction between the "handle wafer" of the SOI wafer and the resonators are major loss mechanisms that decreases the Q-factor.

In order to avoid these drawbacks a supplementary etching process may be used on the back side of the SOI to remove part of the handle wafer under the resonator. The cavity 315, 655 may be etched by DRIE under the resonator. The etching may be continued until the buried oxide is also removed.

A similar cavity 314 can be etched simultaneously under the optic fiber. Thus the fiber can be better fixed and even the vertical positioning of the light beam is adjusted.

The main steps for a complete process flow to manufacture these photo-acoustics detectors are the followings.

First, the piezoelectric structures are manufactured on the "device" side of the SOI wafer. The first metal electrode, the piezoelectric layer and the second metal electrode are deposited and patterned consecutively.

The cavity is etched under the resonators and eventually under the optic fiber position by DRIE on the "handle wafer" side of the SOI wafer. The process is continued until the BOX is completely removed under the cantilever.

Finally the resonators are released by performing the etching of the "device" side of the SOI wafer. It is a DRIE etch through the entire "device" side of the SOI wafer.

In some embodiments, a photo-acoustic gas detector utilizes a resonant structure realized in Silicon. The resonator may be etched by DRIE in SOI wafer.

The light source is a laser coupled to fiber optic in one embodiment. The silicon structure is provided with a groove that is used to embed the fiber. This grove may be etched in same process that is used for releasing the silicon resonator.

In order to reduce the losses due to air friction and air squeezing a hole may be etched by DRIE in the handle wafer from SOI under the resonator.

In order to allow a better fixation of the fiber a hole may be etched by DRIE in the handle wafer under the fiber.

Examples

1. A device comprising:
 a resonator having an oscillating portion;
 a light source to provide light along a length of the oscillating portion; and a detector to detect a change in oscillation of the resonator responsive to the light source heating a gas.
2. The device of example 1 wherein the resonator comprises a micro electro-mechanical systems (MEMS) beam oscillator formed of silicon.
3. The device of example 1 or 2 wherein the resonator comprises a micro electro-mechanical systems (MEMS) tuning fork oscillator.
4. The device of example 3 and further comprising a further light source such that light is directed along outside lengths of two tines of the tuning fork oscillator
5. The device of any of examples 1-4 wherein the resonator comprises a micro electro-mechanical systems (MEMS) T shaped oscillator and wherein the light is directed along a length of a top of the T shaped oscillator.
6. The device of any of examples 1-5 wherein the light source comprises an optical fiber to couple to a laser.
7. The device of example 6 and further comprising a lens to focus light from the optical fiber to minimize dispersion of the light along the length of the resonator.
8. The device of any of examples 1-7 wherein the resonator is formed of silicon.
9. The device of any of examples 1-8 wherein the light is tuned to a resonant frequency of the resonator and to a selected absorption line of the gas to be detected.
10. A method comprising:
 providing light adjacent to a length of a micro electromechanical systems (MEMS) resonant oscillator;
 exposing a gas to be detected to the light to create a pressure wave; and
 detecting oscillation of the oscillator responsive to the pressure wave.
11. The method of example 10 wherein the light has a frequency corresponding to a resonant frequency of the resonant oscillator and to an absorption line of the gas to be detected.
12. The method of example 11 wherein the light source comprises an optical fiber having a diameter similar to a height of the resonator.
13. The method of example 12 wherein the light source further comprises a splitter coupled to the optical fiber and two additional optical fibers to receive light form the splitter and direct the light along a length outside of two tines of a resonant oscillator tuning fork.
14. The method of any of examples 10-13 and further comprising focusing the light along the length of the resonator such that the light does not significantly disperse.
15. The method of any of examples 10-14 wherein the resonator comprises a micro electro-mechanical systems (MEMS) beam oscillator formed of silicon.
16. The method of any of examples 10-15 wherein the resonator comprises a micro electromechanical systems (MEMS) T shaped oscillator and wherein the light is directed along a length of a top of the T shaped oscillator.
17. The method of any of examples 10-16 wherein the light source comprises an optical fiber to couple to a laser.
18. A sensor comprising:
 a device wafer formed of silicon;
 a microelectricalmechanical single crystal resonator released from the silicon on insulator device wafer and having an oscillating portion with a length and a width;
 an optical fiber light source to provide light along the length of the oscillating portion in a cavity formed in the device wafer, the light having a frequency tuned to a resonant frequency of the resonator and to an absorbtion line of a gas to be detected;
 a handle wafer supporting the device wafer and the optical fiber light source; and
 a detector to detect a change in oscillation of the resonator responsive to the light source heating the gas.
19. The sensor of example 18 wherein the detector comprises a piezoelectric layer supported by the resonator to provide a signal representative of deflection of the resonator due to pressure waves from the heated gas.
20. The sensor of example 19 wherein the piezoelectric layer is spit into two portions along the length of the resonator and further comprising a pair of electrodes coupled to respective portions of the piezoelectric layer.

The functions or algorithms for processing collected data, driving a resonator, and controlling laser modulation described herein may be implemented in software or a combination of software and human implemented procedures in various embodiments. The software may consist of computer executable instructions stored on computer readable media such as memory or other type of storage devices. Further, such functions correspond to modules, which are software stored on storage devices, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device comprising:
   a resonator having an oscillating portion formed as a single-prong suspended beam having a supported end;
   a light source to provide light along a length of the oscillating portion, the light being directed toward the supported end; and
   a detector to detect a change in oscillation of the resonator responsive to the light source heating a gas, wherein the detector comprises a piezoelectric layer split into two adjacent portions along the length of the single-prong suspended beam supported by a ground electrode, and further comprises a pair of electrodes extending along the lengths of and coupled to respective adjacent portions of the piezoelectric layer, wherein one electrode is positioned to collect positive electrical charges from one portion of the piezoelectric layer and the other electrode is positioned to collect negative electrical charges from the other portion of the piezoelectric layer, such that the adjacent portions along the length of the single-prong suspended beam prevent charge compensation.

2. The device of claim 1 wherein the resonator comprises a micro electromechanical systems (MEMS) single-prong suspended beam oscillator formed of silicon.

3. The device of claim 1 wherein the light source comprises an optical fiber to couple to a laser.

4. The device of claim 3 further comprising a lens to focus light from the optical fiber to minimize dispersion of the light along the length of the resonator.

5. The device of claim 1 wherein the resonator is formed of silicon.

6. The device of claim 1 wherein the light is tuned to a resonant frequency of the resonator and to a selected absorption line of the gas to be detected.

7. A method comprising:
   providing light adjacent to a length of a micro electromechanical systems (MEMS) cantilever single-prong suspended beam resonant oscillator, the light being provided along the single-prong suspended beam toward a supported end of the beam;
   exposing a gas to be detected to the light to create a pressure wave; and
   detecting oscillation of the single-prong suspended beam resonant oscillator responsive to the pressure wave via a detector having a piezoelectric layer split into two adjacent portions supported by a ground electrode, along the length of the single-prong suspended beam resonant oscillator and further comprising a pair of electrodes extending along the lengths of and coupled to respective adjacent portions of the piezoelectric layer, wherein one electrode is positioned to collect positive electrical charges from one portion of the piezoelectric layer and the other electrode is positioned to collect negative electrical charges from the other portion of the piezoelectric layer, such that the adjacent portions along the length of the single-prong suspended beam resonant oscillator prevent charge compensation.

8. The method of claim 7 wherein the light has a frequency corresponding to a resonant frequency of the single-prong suspended beam resonant oscillator and to an absorption line of the gas to be detected.

9. The method of claim 8 and further including performing calibration of the single-prong suspended beam resonant oscillator by:
   driving the single-prong suspended beam resonant oscillator via one of the electrodes and corresponding portion of the piezoelectric layer; and
   sensing movement of the single-prong suspended beam resonant oscillator via the other one of the electrodes and corresponding other portion of the piezoelectric layer.

10. The method of claim 7 and further comprising focusing the light along the length of the single-prong suspended beam resonant oscillator such that the light does not significantly disperse.

11. The method of claim 7 wherein the single-prong suspended beam resonant oscillator is formed of silicon.

12. The method of claim 7 wherein the light source comprises an optical fiber to couple to a laser.

13. The method of claim 7 and further comprising subtracting signals on the electrodes from each other to provide an output signal representative of the movement of the single-prong suspended beam resonant oscillator.

14. A sensor comprising:
   a device wafer formed of silicon;
   a microelectricalmechanical single crystal cantilevered single-prong beam resonator released from the silicon on insulator device wafer and having a single-prong beam oscillating portion with dimensions chosen to lead to a desired resonant frequency;
   an optical fiber light source to provide light along the length of the oscillating single-prong beam portion in a cavity formed in the device wafer, the light having a frequency tuned to a resonant frequency of the resonator and to an absorption line of a gas to be detected, and wherein the light is directed toward a supported portion of the cantilevered single-prong beam;
   a handle wafer supporting the device wafer and the optical fiber light source; and
   a transducer to detect a change in oscillation of the single-prong beam resonator responsive to the light source heating the gas, wherein the transducer comprises a piezoelectric layer split into two adjacent portions supported by a ground electrode, along the length of the single-prong beam resonator and further comprising a pair of electrodes extending along the lengths of and coupled to respective adjacent portions of the piezoelectric layer, wherein one electrode is positioned to collect positive electrical charges from one portion of the piezoelectric layer and the other electrode is positioned to collect negative electrical charges from the other portion of the piezoelectric layer, such that the adjacent portions along the length of the single-prong beam of the resonator prevent charge compensation.

* * * * *